United States Patent [19]
Paukkunen et al.

[11] Patent Number: 5,557,042
[45] Date of Patent: Sep. 17, 1996

[54] IMPEDANCE DETECTOR, IN PARTICULAR FOR RADIOSONDE OPERATION, AS WELL AS A PROCESS FOR THE MANUFACTURE OF A DETECTOR

[75] Inventors: Ari Paukkunen, Vantaa; Jorma Ponkala, Ylönkylä, both of Finland

[73] Assignee: Vaisala Oy, Vantaa, Finland

[21] Appl. No.: 412,142

[22] Filed: Mar. 28, 1995

Related U.S. Application Data

[62] Division of Ser. No. 307,057, Sep. 16, 1994.

[30] Foreign Application Priority Data

Sep. 29, 1993 [FI] Finland ................................... 934266

[51] Int. Cl.$^6$ ........................... G01N 27/04; G01W 1/00; G01R 27/26
[52] U.S. Cl. .................... 73/335.03; 73/29.02; 73/29.05; 29/25.42; 29/825; 427/79; 324/664; 324/689
[58] Field of Search ............................. 73/335.03, 29.02, 73/29.05, 335.04, 29.01, 335.03, 335.02; 29/825, 25.42; 427/79, 80; 324/689, 29.01, 664

[56] References Cited

U.S. PATENT DOCUMENTS

| | | | |
|---|---|---|---|
| 2,011,710 | 8/1935 | Davis | 29/25.42 |
| 3,075,385 | 1/1963 | Stover | 73/29.02 |
| 3,168,829 | 2/1965 | Nelson | 73/335.04 |
| 3,350,941 | 5/1965 | Misevich et al. | 73/335.04 |
| 3,443,293 | 5/1969 | Masujima | 29/25.42 |
| 3,559,456 | 2/1971 | Lomker et al. | 73/29.05 |
| 4,347,550 | 8/1982 | Rockliff | 361/286 |
| 4,723,439 | 2/1988 | Asakura et al. | 73/29 |
| 4,793,181 | 12/1988 | Djorup | 73/336.5 |
| 4,891,574 | 1/1990 | Nagaya et al. | 324/61 P |
| 4,991,055 | 2/1991 | Marneffe et al. | 361/321 |
| 5,018,048 | 5/1991 | Shaw et al. | 361/323 |
| 5,036,704 | 8/1991 | Pusatcioglu et al. | 73/336.5 |
| 5,156,045 | 10/1992 | Ponkala | 73/170 R |
| 5,179,773 | 1/1993 | Monsees et al. | 29/25.42 |
| 5,355,569 | 10/1994 | Marek et al. | 29/25.41 |

FOREIGN PATENT DOCUMENTS

| | | | |
|---|---|---|---|
| 48229 | 1/1974 | Finland | 73/29 |
| 4140831A1 | 7/1993 | Germany. | |
| 0135945 | 8/1983 | Japan | 73/335.03 |
| 597955 | 3/1978 | U.S.S.R. | 73/335.03 |
| 2234820 | 8/1990 | United Kingdom. | |

OTHER PUBLICATIONS

FI–48229 (with English claims).
FI–933701 (English translation only).
FI–933702 (English translation only).
Japanese Abstract JP–A–57–201827, Dec. 10, 1982.

*Primary Examiner*—Hezron E. Williams
*Assistant Examiner*—J. David Wiggins
*Attorney, Agent, or Firm*—Jones & Askew

[57] ABSTRACT

An impedance detector, in particular for radiosonde operation. The detector comprises a substrate (10 ... 10E) made of an insulating material, onto which substrate the electrode and contact patterns (11, 11a, 13) necessary for the formation and connecting of the detector impedance have been applied. Between the detector impedance electrodes (11, 13), there is an active film (12), whose impedance values are a function of the physical quantity measured by means of the detector. The substrate of the detector is an oblong core filament (10; 10B; 10C; 10D; 10E) of an insulating material, onto and around which core filament said electrodes (11, 13) and said active insulating film (12) have been applied. Also, a novel process is described for the manufacture of said impedance detector.

6 Claims, 5 Drawing Sheets

FIG. 11 a division of application Ser. No. 08/307,057, filed Sep. 16, 1994.

IMPEDANCE DETECTOR, IN PARTICULAR FOR RADIOSONDE OPERATION, AS WELL AS A PROCESS FOR THE MANUFACTURE OF A DETECTOR

This is a division of application Ser. No. 08/307,057, filed Sep. 16, 1994.

The invention concerns an impedance detector, in particular for radiosonde operation, which detector comprises a substrate made of an insulating material, onto which substrate the electrode and contact patterns necessary for the formation and connecting of the detector impedance have been applied, and in which detector, between the detector impedance electrodes, there is an active film, whose impedance values are a function of the physical quantity measured by means of the detector.

The invention concerns a process for the manufacture of an impedance detector.

In the prior art, a number of different electrically detected temperature and humidity detectors are known whose impedance changes as a function of the quantity to be measured. Such humidity detectors are known, e.g., from the U.S. Pat. Nos. 3,168,829 and 3,350,941 and from the applicant's Finnish Patent No. 48,229.

The FI Patent No. 48,229 is related to the prior art concerned in the present invention, in which patent a capacitive humidity detector is described in which the dielectric insulating material is a polymer film whose permittivity is a function of the amount of water absorbed by the polymer film.

As is known in the prior art, also for measurement of temperature, capacitive detectors are used, which are usually based on the fact that the permittivity of the insulating material between the capacitor plates is dependent on the temperature, in which case the capacitance detected from the terminals of the detector also depends on the temperature.

In the detectors described above and also in other detectors based on change in impedance, undesirable phenomena occur, which include freezing and wetting of detectors, radiation error, slowness of the detectors, and hysteresis.

In order to solve the problems discussed above, it is known from the prior art to provide said detectors with various mechanical shields. Also, attempts have been made to prevent the problems by providing the detectors with heating. Heated detectors require precise measurement of the temperature, which, for its part, produces problems of its own.

With respect to the most recent development work carried out by the applicant, related to and closely connected with the present invention, reference is made to the following FI Patent Applications: No. 921449 (filed Apr. 1, 1992), No. 933701 (filed Aug. 23, 1993) and No. 933702 (filed Aug. 23, 1993). The constructions and methods described in said applications can, where applicable, also be used in combination with the present invention.

Moreover, in the prior-art humidity detectors, there has been need of further development in respect of the speed and accuracy of the detectors.

The prior-art processes of manufacture of the detectors concerned have been demanding and consisted of a number of steps, in particular when a detector of maximum rapidity and accuracy has been aimed at, which usually requires very small size and precise measures of the constructions as well as good control of the various parameters in the processes of manufacture.

The object of the present invention is further development both of the constructions and of the processes of manufacture of the prior-art impedance detectors, in particular of humidity detectors, so as to avoid the drawbacks mentioned above and to achieve the objectives stated above and those that will come out later.

For these purposes, the detector in accordance with the invention is mainly characterized in that the substrate of the detector is an oblong core filament of an insulating material, onto and around which core filament said electrodes and said active film have been applied.

On the other hand, the process of manufacture of said detectors in accordance with the invention is mainly characterized in that the process comprises a combination of the following steps (a), (b), (c), and (d) carried out in the given sequence:

(a) onto the continuous core filament of insulating material, conductive bottom electrodes are vapour-deposited at a certain mutual axial distance from one another;

(b) the continuous core filament obtained in the step (a) is coated with a material active in the measurement of impedance;

(c) the continuous core filament obtained in the step (b) is coated with conductive surface electrodes, which are at least partly placed facing the gaps between said bottom electrodes and at least partly facing the bottom electrodes, and (d) the continuous detector filament obtained from the step (c) is cut off into pieces to make the impedance detectors.

When the invention is applied as a capacitive humidity detector, the active material is an insulating material whose permittivity is a function of the amount of water absorbed by the insulating material.

The impedance detector in accordance with the invention is characterized by wire-shaped form, small size, and little mass, which contributes to a detector of rapid time responses. The circular cross-sectional shape and the small size of the detector are also of advantage in the elimination of the freezing phenomenon. The little and favourable forms in the detector may already be sufficient to eliminate the problem of condensing and freezing of humidity, if necessary, together with a particular surface treatment. However, if these means are not sufficient, it is possible to integrate the detector in accordance with the invention with an efficient and rapid heating, in which case the measurement of temperature required in a humidity detector is precise and quick, because the inside and outside heat transfer properties of the detector are favourable. In such a case, measurement of temperature is used, in the way known from the prior art, as a starting value in the correction computing to eliminate the effect of heating that distorts the measurement of humidity.

The detector construction that is most appropriate in each particular case depends on the mode of application of the detector in accordance with the invention. The detector can be used while heated constantly, periodically, or in some other way under controlled heating. The humidity detector in accordance with the invention is suitable for the use of efficient heating pulses of a duration of an order of just a millisecond, in which case quick measurement applications are possible. The measurement of temperature may take place as continuous or while alternating with measurement of humidity. With respect to cyclic heating and measurement of temperature, reference is made to the applicant's said FI Pat. Appl. 933702. It is also possible to accomplish the detector construction of the invention without heating and without measurement of temperature. Detector protection is not needed necessarily because of the small size of the detector. The shield constructions in themselves are centres of condensing and produce problems of humidity measurement.

The detector construction in accordance with the invention permits the use of a continuous filament reel process in its manufacture and makes it easy to cut the filament into detector pieces and to use said detectors when provided with contacts at their ends. The core filament may be formed in a number of different ways. It is possible to use fibreglass alone, or in the interior of the glass there may be a heating resistor and/or a temperature measurement detector. For a temperature meter, a miniature thermistor is also suitable. The glass itself may also operate as the dielectric of a capacitive temperature detector, in which the core filament may be, at the same time, the heating resistor and one of the electrodes of the temperature measurement capacitance, whereas the metallization placed on the core constitutes the other electrode. As the basic material of the core, it is also possible to use some other suitable material besides glass, such as plastic.

In the process of manufacture of the invention, onto the core filament, thin metal areas are vapour-deposited, which areas operate as a combined bottom and contact electrode when the detector is connected to its environment. Onto this construction, a thin polymer film or equivalent is processed. Onto this plastic film, the surface electrode is vapour-deposited, through which electrode moisture can penetrate into the polymer film. The surface electrode is preferably placed so that it is placed partly overlapping two successive bottom electrodes, and the part of the bottom electrode that is not covered by a surface electrode operates as a contact area when the detector is connected to its environment. Constructions of a different sort are also possible within the scope of the invention. The electrodes do not have to be unified faces and extend around the whole core, but they may consist of two or even more than two parts.

In particular when manufactured by means of the process of the present invention, the detector in accordance with the invention becomes of low cost and easy to use. The detector in accordance with the invention is particularly suitable for use in radiosondes in measurement of relative humidity, but the humidity detector in accordance with the invention can also be applied to measurement of humidity in industry also under demanding conditions, and for weather monitoring or equivalent on the ground. In this connection, it should, however, be emphasized that the scope of the invention also includes other detectors, besides capacitive humidity detectors, such as resistive or capacitive temperature detectors and other, corresponding impedance detectors.

Increased length and reduced thickness of the detector filament usually improve the construction of the humidity detector, because by these means the radiation error can be reduced, and an interfering adhesion of a water drop becomes more difficult and, even if a water drop should adhere, its relative effect of increasing the area of the surface electrode is reduced.

If a heating wire and/or a temperature measurement wire is used inside the core filament in the detector filament in accordance with the invention, the gaps between the bottom electrodes should be dimensioned as little as possible so that the formation of a capacitance between the surface electrode and the wire placed in the core is minimized.

In the following, the invention will be described in detail with reference to different exemplifying embodiments of the invention illustrated schematically in the figures in the accompanying drawing, the invention being by no means strictly confined to the details of said embodiments.

To begin with, mainly with reference to FIGS. 1, 2A, 2B, and 2C, the principal features of the process of manufacture and of the detector in accordance with the invention will be described briefly.

By means of the process in accordance with the invention, a continuous detector filament 100 is manufactured. Out of this detector filament 100, pieces are cut off in the transverse direction at the points R—R, which pieces constitute finished humidity detectors after making of possible connector parts. The humidity detector is processed onto a thin core filament 10, which acts as the substrate of the detector. The core filament 10 is by nature of circular section, and its diameter $D_s \approx 2r_s$ is very little, being, as a rule, in the range of $D_s \approx 10$ μm ... 2 mm, in radiosonde applications preferably in the range of $D_s \approx 50$ μm ... 200 μm. Onto the core filament 10, in the areas F indicated in FIG. 1, bottom electrodes 11 have been applied, which also operate as contact parts. Onto the bottom electrodes 11 and onto the parts of core filament 10 that remain free from said electrodes, a polymer film 12 or equivalent has been applied. The polymer film 12 operates as an active part in the detector capacitance $C_M$. The permittivity e of the polymer film 12 is a function of the amount of water absorbed by the polymer film 12, so that $C_M$=f(RH). Onto the polymer film 12, in the areas P, a surface electrode 13 has been applied, which is so thin that it is penetrable by moisture but is, however, electrically continuous. The detector filament 100 is cut off into pieces in the middle of the area F of the bottom electrodes 11, and in the areas E the polymer film 12 is removed so that connector areas are formed, to which the capacitance CM measurement wires are connected.

Figure 1:
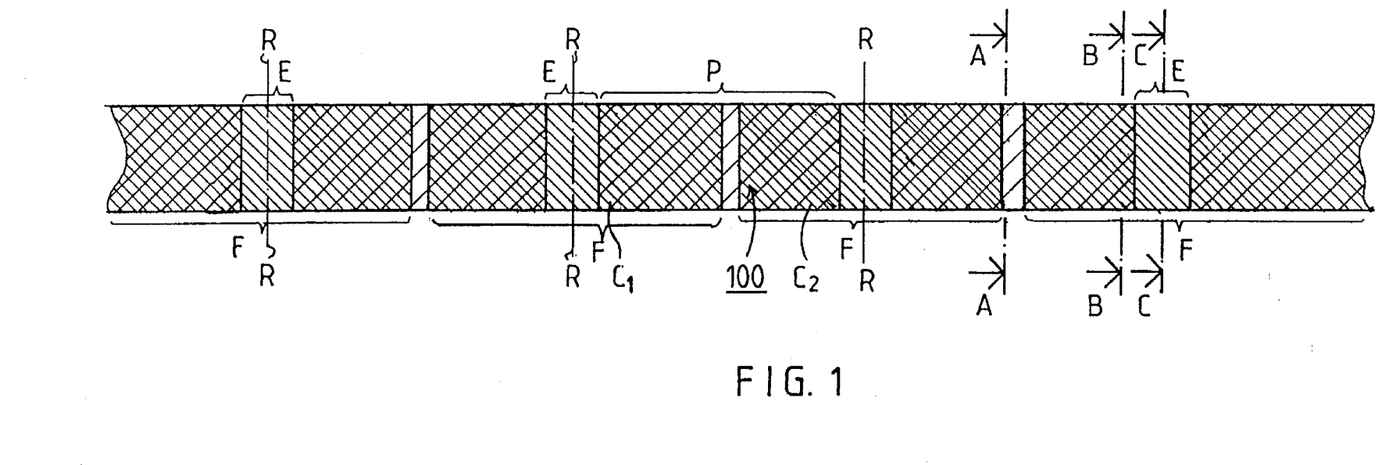
FIG. 1 is a schematic illustration of a detector filament manufactured by means of the process of the invention, from which filament the detectors in accordance with the invention are cut off.
Figure 2A:
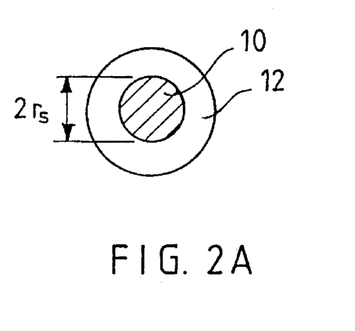
FIG. 2A is a sectional view taken along the line A—A in FIG. 1.
Figure 2B:
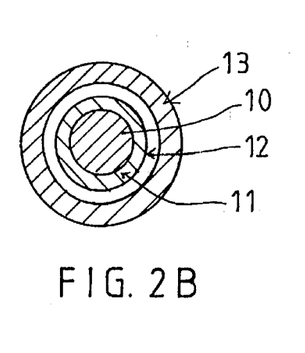
FIG. 2B is a sectional view taken along the line B—B in FIG. 1.
Figure 2C:
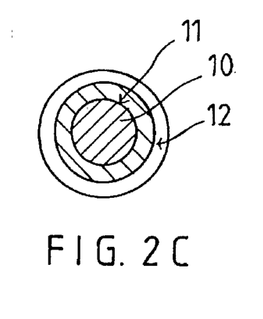
FIG. 2C is a sectional view taken along the line C—C in FIG. 1.

According to FIG. 1, in the areas $C_1$ and $C_2$, between the bottom electrode 11 and the surface electrode 13, capacitances are formed, whose dielectric is the polymer film 12.

Figure 3A:
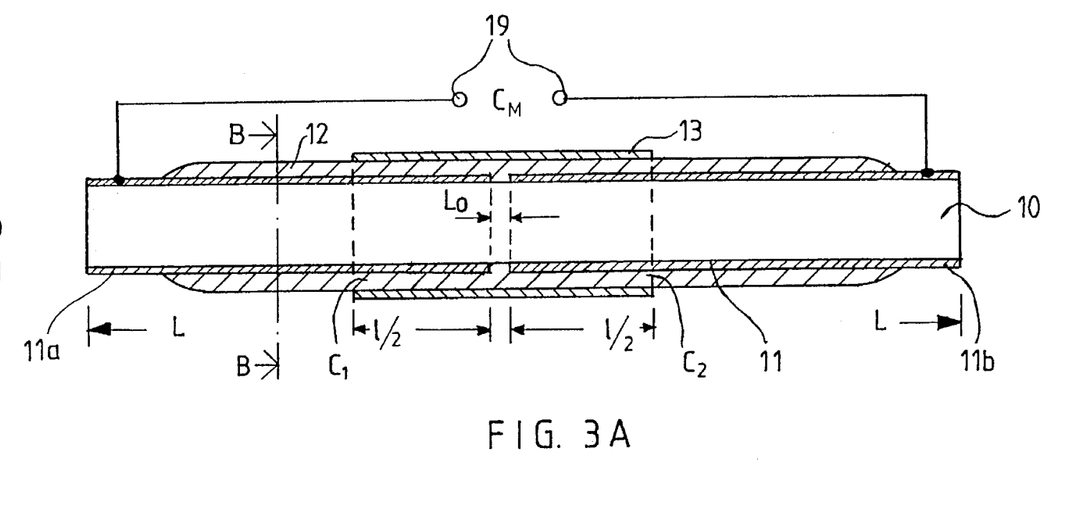
FIG. 3A is a central longitudinal sectional view of a preferred detector construction in accordance with the invention.

In the following, with reference to FIGS. 3A and 3B, a preferred exemplifying embodiment of the construction and dimensioning of the detector in accordance with the invention as well as the principle of operation of the detector will be described. The cylindrical capacitors $C_1$ and $C_2$ formed in the areas of both ends of the surface electrode 13 are connected in series when the detector capacitance $C_M$ is measured between the terminals 19. With the measures given in FIG. 3A, $C_1$=$C_2$=C, in which case $C_M$=C/2. In the construction of FIG. 3A, the active length l of the detector can be divided between the component capacitances $C_1$ and $C_2$ also in some way other than ½ and ½, i.e. the capacitances $C_1$ and $C_2$ can be of different magnitudes, compared with each other, which may be even an advantage, because in such a case a connection with the ground is not so disturbing.

The capacitance C of a cylindrical capacitor is theoretically:

$$C = \frac{2\pi\epsilon l}{\ln\frac{r_u}{r_s}}$$

wherein:

$\epsilon$=permittivity of the medium l=length $r_u$ and $r_s$=outer and inner radii Typically, the dielectric constant. $\epsilon_r$ ($\epsilon=\epsilon_r\epsilon_o$) is in the range of $\epsilon_r \approx 2 \ldots 5$. The thickness of the polymer film 12, i.e. $r_u$-$r_s$, is typically a few micrometers.

In each detector application, the detector capacitance $C_M$ can be dimensioned in accordance with the requirements of the particular application mainly by varying the axial measure 1.

In the following, the widest ranges of variation of different parameters in the dimensioning of a humidity detector and the preferable ranges of variation of same in radiosonde applications will be given.

Figure 3B:
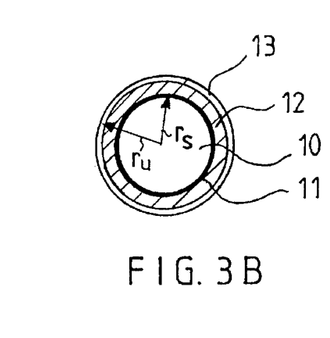
FIG. 3B is a sectional view taken along the line B—B in FIG. 3A.

$r_s \approx 5$ μm ... 1 mm, preferably $r_s \approx 25$ μm ... 100 μm $r_u \approx 5$ μm ... 1 mm, preferably $r_u \approx 25$ μm ... 100 μm l≈0.01 mm ... 100 mm, preferably l≈0.1 mm ... 40 mm $L_0 \approx 0.1$ mm, ... mm, preferably $L_0 \approx 0.5$ mm ... 5 mm L≈0.1 cm ... 20 cm, preferably L≈1 cm ... 10 cm The capacitance $C_M$ measured from the terminals 19 of the detector as shown in FIGS. 3A and 3B is $C_M \approx 0.1$ pF ... 1000 pF, in radiosonde applications preferably $C_M \approx 2$ pF ... 500 pF.

In the following, with reference to FIGS. 4A to 4E, different alternative constructions of the core filament 10 which forms the substrate of the detector in accordance with the invention will be described. According to FIG. 4A, the core filament 10 is a thin fibre made of glass or of some other insulation material alone. According to FIG. 4B, in the core filament 10B, there is a resistor wire 14 that has been processed into the fibreglass core 10a, which resistor wire can be used as a heating resistor for the detector and/or for measurement of the temperature of the detector. In the core filament 10C shown in FIG. 4C, the core 10b is made of dielectric ceramic glass, which acts as the dielectric in the measurement of the temperature of the detector. The outside layer 16 consists of a glass coating or of some other insulating layer. With respect to the details of this construction, reference is made to the applicant's FI Patent Application No. 921449 of earlier date (filed Apr. 1, 1992). In the core filament 10D shown in FIG. 4D, in the interior of the fibreglass core 10a, two parallel heating resistor wires 14a and 14b are fitted, which operate as resistances for the heating of the detector and/or for measurement of the temperature. The outer layer consists of glass or of some other insulating layer 16.

Figure 4A:
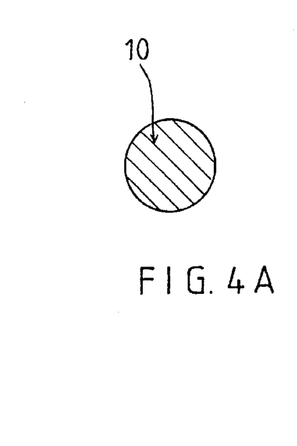
FIGS. 4A, 4B, 4C, 4D, and 4E are sectional views that illustrate alternative different constructions of the core filament that is used in the process of manufacture of the invention.
Figure 4B:
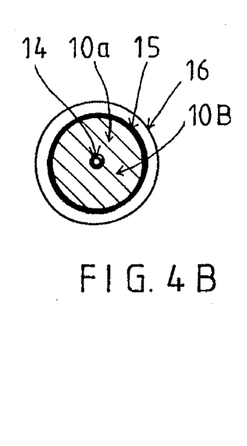
Figures 4C, 4D:
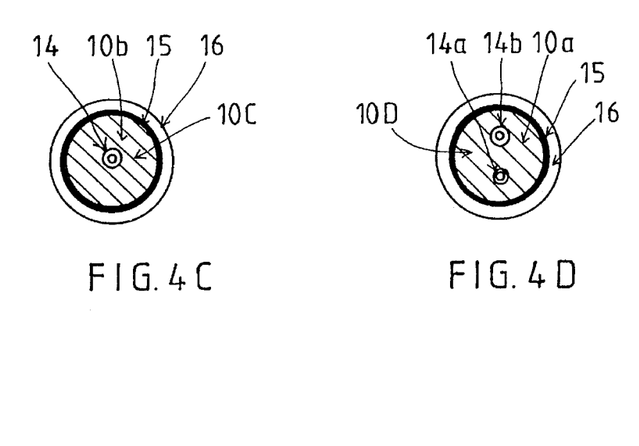
Figure 4E:
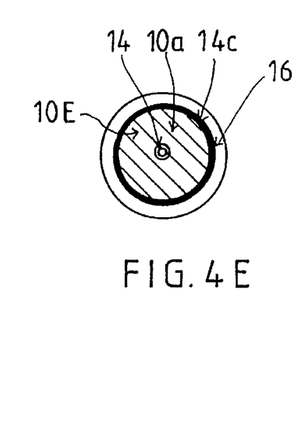

In the core filament 10E shown in FIG. 4E, inside the glass core 10a there is a heating resistor wire 14, and outside the glass core 10 a resistor wire 14c has been wound for the purpose of measurement of the temperature. The functions of the resistor wires 14 and 14c may also be reversed. The outer layer 16 is a metallized layer or a glass coating. The wire 14c may be a suitable metal wire, such as a platinum wire.

With respect to FIGS. 4A to 4E, it should still be emphasized that therein expressly core filaments 10; 10B, 10C; 10D; 10E are shown that operate as the substrate of the detector, onto which filaments the bottom electrodes 11, the polymer film 12, and the surface electrodes 13 are processed further. With respect to the details of the construction and of the processes shown in FIG. 4C, in which a dielectric ceramic glass is used as the core 10b, reference is made to the applicant's said FI Pat. Appl. No. 921449. In the construction shown in FIG. 4C, the measurement of the capacitance of the detector, which depends on the temperature, can be carried out between two opposite electrodes 15, as is described in said FI patent application, or between a cylindrical electrode 15 and a central electrode, which central electrode may also consist of a resistor wire 14. It is also possible to use various combinations and mixed constructions in accordance with FIGS. 4B to 4E.

Figure 5:
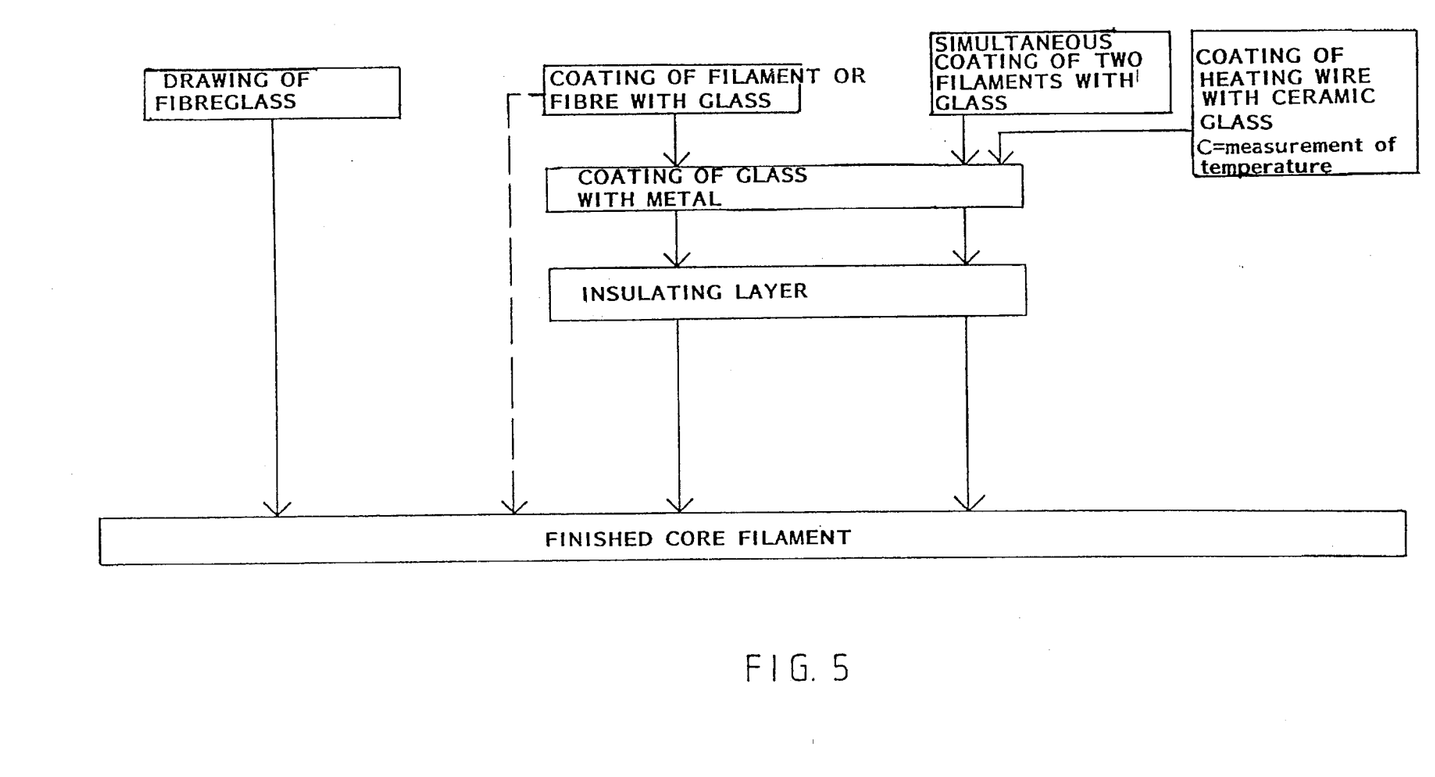
FIG. 5 is a block diagram illustration of different steps of manufacture of the core filament that is used in the detector in accordance with the invention.

FIG. 5 shows the production process of the core filament as a block diagram. The drawing of fibreglass is based on technology in itself known. So also the coating of a filament with glass, e.g., by means of a crucible with a hole, in which molten glass and the filament are drawn through the hole. It is also possible to coat two filaments with glass by means of a similar crucible so that the filaments remain separate inside the glass. The coating with glass can also be carried out by means of glass paste. The coating of fibreglass with metal can be carried out as vacuum evaporation or by means of conductive pastes. An insulating layer can be applied onto a metal-coated glass, e.g., by means of a perforated crucible with low-melting glass or by paste coating or by chemical methods, and some other insulating layer can be applied by submerging in a liquid.

Figure 6:
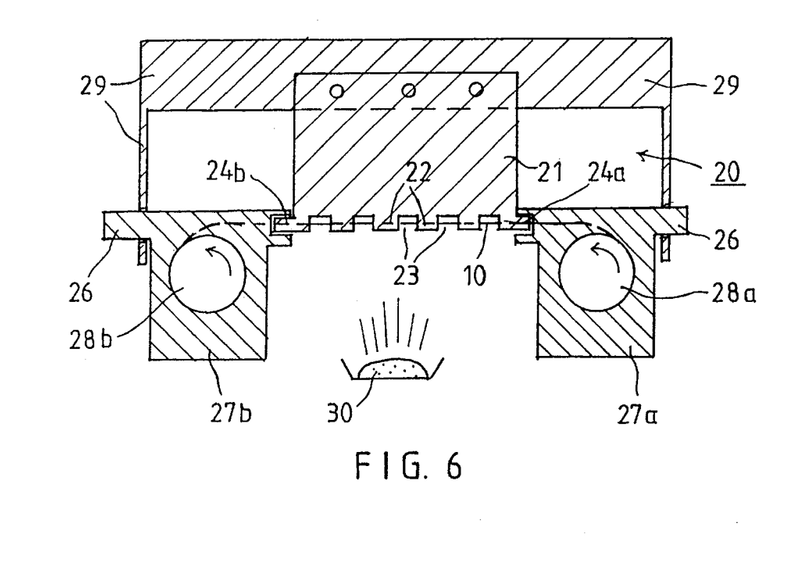
FIG. 6 is a schematic illustration of a vapour-deposition device which is provided with reeling and rotating parts and which is intended for making the bottom electrodes in the process of manufacture in accordance with the invention.
Figure 7A:
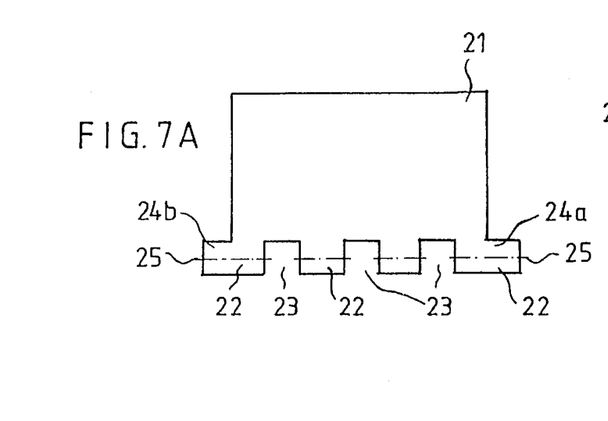
FIG. 7A shows the mask part in the device as shown in FIG. 6.
Figure 7B:
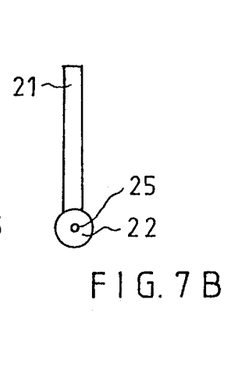
FIG. 7B shows the same as FIG. 7A, seen in the direction of the guide opening of the mask part.
Figure 8:
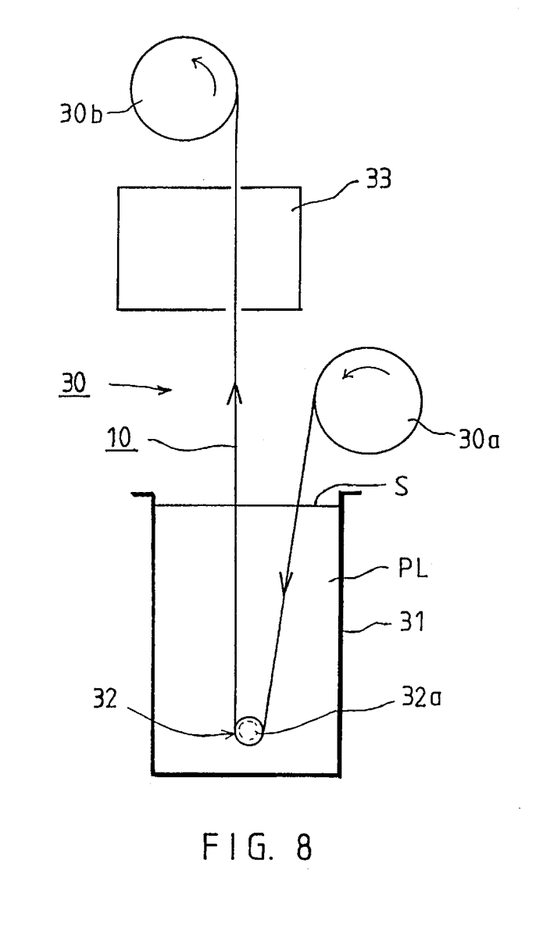
FIG. 8 is a schematic illustration of a continuous device based on reefing of a fibre and used in the process of manufacture in accordance with the invention, by means of which device the fibre filament provided with electrodes is coated with an active polymer film.

In FIGS. 6 to 8, some devices are illustrated schematically by whose means a core filament 10 produced in accordance with FIG. 5 can be provided with bottom electrodes 11 and be coated with an active polymer coating or equivalent.

Onto the core filament 10, bottom electrodes 11 are vapour-deposited out of metal, which electrodes also operate as contact areas with the environment of the detector. The vacuum evaporating takes place, for example, so that the filament runs, in the way shown in FIG. 5, from the reel 28a onto the reel 28b stepwise as transfers of invariable length. Between the reels 28a and 28b, the filament 100 is straight and runs through the evaporation mask 21. The function of the mask 21 is to protect the areas of the filament 10 that are not coated with metal. In order that the metallization could be applied around the filament 10, the filament 10 can be either rotated around its longitudinal axis in the mask 21, or several sources 30 of evaporation are used. In FIG. 6, for said rotation of the filament 10, the reels 28a, 28b are mounted on frame parts 27a and 27b, which are again mounted by means of horizontal shafts 26 and by means of axle journals 24a, 24b fitted at the ends of the mask part 21 so that they can rotate around a horizontal axis, which horizontal axis coincides with the series of holes 25 in the mask 21 through which the filament 10 is passed from the starting reel 28a to the arrival reel 28b. In principle, the evaporation mask 21 is a number of pipes 22, which are placed at an invariable distance from one another. The filament 10 passes through the series of holes 25 in the pipe pieces 22, and the metallization is produced in the gaps in which the pipes 22 do not protect the filament. The metal evaporation takes place as vacuum evaporation from a source 30, so that the equipment 20 is placed inside an evaporation hood 29. Further, if necessary, the equipment 20 includes an optical detector as an aid for the mask alignment.

The filament 10 produced in the step of detector manufacture shown in FIGS. 6 and 7 is coated in the device 30 shown in FIG. 8 with a thin polymer layer, whose polymer PL operates as the humidity-sensitive insulation material of the capacitive detector that is formed, the permittivity of said material being a function of the amount of water absorbed by the film. The coating takes place by transferring the filament 10 from the reel 30a onto the reel 30b at an invariable speed. Between the reels 30a and 30b, the filament 10 is submerged in polymer PL in the basin 31, which contains a suitable solution concentration. In the bottom part of the basin 31, there is a guide roll or rod 32, over whose groove 32a the filament 10 is guided in the basin 31 first down and then up. Drying takes place in an oven 33 before the arrival reel 30b of the filament 10. The polymer PL can also be applied onto the filament by using a crucible through which the filament is drawn.

Onto the filament 10 obtained in the step of manufacture shown in FIG. 8, the surface electrodes 13 are vapour-deposited in the same way as the bottom electrodes 11 were deposited in the step shown in FIGS. 6 and 7. At the beginning, the location of the surface electrode 13 is aligned correctly between two bottom electrodes 11 and partly overlapping said bottom electrodes.

After the latter step, the complete detector filament 100 is cut off at the points R—R, in the middle of the bottom electrodes 11, to make the detectors (FIG. 1). If the detector filament 100 comprises detector elements, various peeling processes, etchings, etc. are needed in order that the contact areas could be uncovered from the core. The peeling can take place, e.g., by etching, for example by means of a system similar to that shown in FIG. 8. The electric connecting of the detector takes place primarily by means of an electrically conductive adhesive. As a shield, preferably epoxies can be used. In the making of the detector, a number of different process steps may be needed additionally, for example treatments in an oven, chemical coatings, etchings, etc. They may be carried out by means of devices similar to those shown in FIGS. 6 and 8.

Well suitable for the material of a heating wire 14 is, for example, platinum. The resistance of the heating resistor 14 is, as a rule, in the range of 1 ... 5000 ohm, preferably 1 . . . 1000 ohm. The resistance of a wire that is used for measurement of temperature, for example a platinum wire, is, as a rule, in the range of 1 ... 3000 ohm, preferably 10 ... 1000 ohm. When capacitive temperature measurement is used, the range of capacitance is typically of the same order as in humidity measurements.

Figure 9:
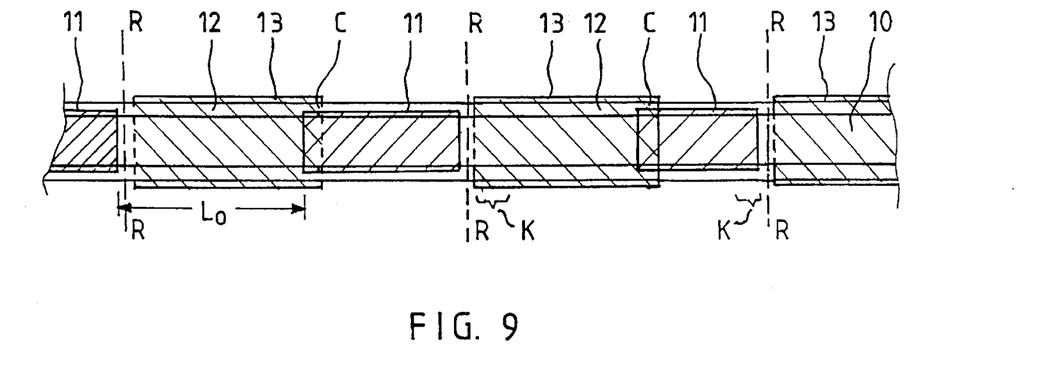
FIG. 9 is a central longitudinal sectional view of a second detector filament manufactured by means of the process in accordance with the invention, from which filament the detectors in accordance with the invention can be cut off.

In FIG. 9, an alternative detector filament is shown which has been manufactured by means of the method in accordance with the invention and out of which pieces of detector filament are cut off at the points R—R between the bottom electrode 11 and the surface electrode 13. The cylindrical bottom electrode 11 and the corresponding coaxial surface electrode 13 are placed one inside the other at one of their ends so that a cylindrical detector capacitance C is formed, in which a polymer film 12 or equivalent constitutes the dielectric. The detector capacitance C is connected by, at one end of the piece of detector filament, uncovering the bottom electrode 11 in the area K, and the connection to the surface electrode 13 takes place from the corresponding end of the piece of detector filament in the area K.

Figure 10:
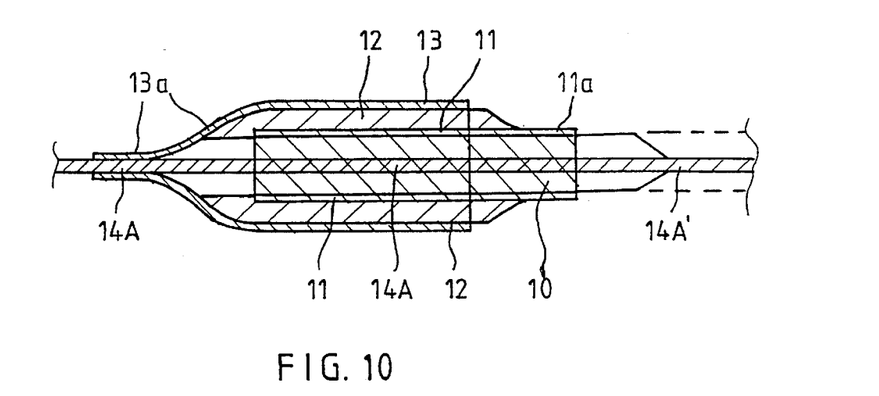
FIG. 10 is a central axial sectional view of a version of the detector in accordance with the invention that is provided with a central wire.

In FIG. 10, inside the filament 10 of insulating material, there is a conductive core wire 14A, to which the surface electrode 13 is connected electrically at one of its ends 13a. The point 13a and the cutting point placed at the vicinity of the core wire 14A are protected, e.g., by means of epoxy or equivalent. The connecting of the detector as shown in FIG. 10 takes place from one end 14A' of the core wire 14A and from the uncovered end 11a of the bottom electrode 11. The active polymer film 12 or equivalent may also extend to outside the surface electrode 13.

Figure 11:
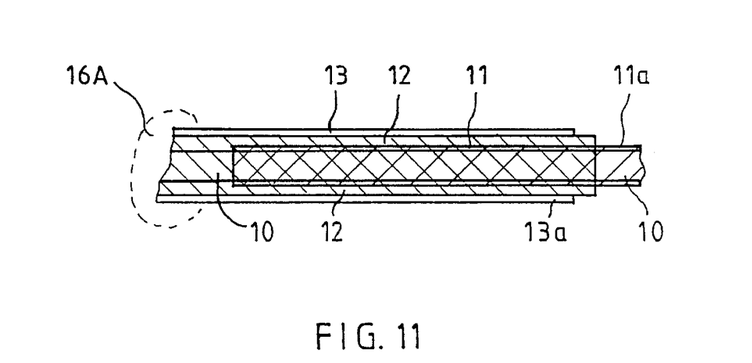
FIG. 11 is a central axial sectional view of a coaxial detector construction in accordance with the invention.

FIG. 11 shows a coaxial detector construction in which one end 16A of the piece of detector filament is protected from humidity by means of epoxy or equivalent. On the core 10, there is a cylindrical bottom electrode 11, and on said electrode a cylindrical active film 12, and on the film a cylindrical surface electrode 13. The parts 10,11,12 and 13 are coaxial with one another. The electric connecting takes place from the ends 11a and 13a of the electrodes 11 and 13. The connection area must be protected from humidity after the electric connecting by means of epoxy or equivalent. In FIG. 10, if the core wire 14A is not needed for measurement of humidity, it can be used for heating the detector and/or for measurement of the temperature. The constructions shown in FIGS. 10 and 11 provide the advantage that the electric connecting of the detector can be carried out from one end of the detector alone, which facilitates the connecting of the detector to its environment. The connecting can be carried out, e.g., by means of an electrically conductive adhesive, in which case it is also possible to use adhesives that are, at the same time, etched through the dielectric layer 12, or said layer can be removed otherwise.

Above, some exemplifying embodiments have been described, which are preferable according to the present experience and estimate. However, it should be emphasized that the idea of the invention can also be carried into effect in a number of manners differing from the exemplifying embodiments given above. The detector filament 100 can also be manufactured so that each piece of detector filament has pairs of bottom electrodes 11 of its own, between whose outer ends there is a free gap, at which the cutting (R—R) of the detector filament 100 is carried out. Also, the bottom electrodes 11 and the surface electrodes are not necessarily unified cylindrical parts, but they may consist of patterns of other sorts and even of separate component patterns.

In the following, the patent claims will be given, and the various details of the invention may show variation within the scope of the inventive idea defined in said claims and differ from what has been stated above by way of example only.

We claim:

1. A capacitive humidity detector intended for radiosonde operation, comprising:
    a substrate (10 . . . 10E) made of an insulating material, onto which substrate are applied electrode and contact layers (11, 11a, 13) necessary for the formation and connecting of the detector, capacitance;
    between the detector capacitance electrodes (11, 13), there is an insulating and active film (12), whose electrical permittivity ($\epsilon$) is a function of the amount of water absorbed by the active film;
    the substrate of the detector is an elongate solid core filament (10; 10B; 10C; 10D; 10E), onto and around which core filament said electrodes (11, 13) and said active and insulating film (12) are applied;
    the diameter $D_s$ of said filament (10; 10B; 10C; 10D; 10E) is in the range of $D_s \approx 10$ µm . . . 2 mm; and
    the detector capacitance is in the range of $C_M \approx 0.1$ pF . . . 1,000 pF.

2. Detector as claimed in claim 1, characterized in that, in a circular section of said core filament (10 . . . 15), the detector is substantially circularly symmetric and, in relation to the longitudinal centre axis of the detector filament (10), substantially coaxial.

3. Detector as claimed in claim 1, characterized in that, on the core filament (10), there are cylindrical bottom electrodes (11), which are placed at a certain distance ($L_0$) from one another in the longitudinal direction of the core filament so that, on said bottom electrodes (11), there is an insulating film (12), and that, on said insulating film (12), there is a cylindrical surface electrode (13), which is so thin that it is penetrable by humidity but is electrically continuous, that said bottom electrodes (11) and said surface electrode (13) extend so that they overlap each other partially on a certain axial dimension (1), that the capacitance ($C_M$) to be measured is formed from a connection in series of the two cylindrical capacitances ($C_1$, $C_2$) between the bottom electrodes (11) and the surface electrode (13), and that the capacitance ($C_M$) to be measured can be measured between said bottom electrodes (11), preferably between their end areas (11a).

4. Detector as claimed in claim 1, characterized in that, in the interior of the core filament (10B; 10C; 10D; 10E), one or several resistor wires (14; 14a, 14b) are fitted, which can be used for electric heating of the detector and/or for measurement of the detector temperature based on the dependence of the resistance of said resistor wire (14; 14a, 14b) on temperature.

5. Detector as claimed in claim 1, characterized in that, on and around the core filament (10E), there is a winding resistor wire that can be used for heating and/or for measurement of temperature (FIG. 4E).

6. The capacitive humidity detector of claim 1 characterized in that the diameter $D_s \approx 50$ µm . . . 200 µm and that the detector capacitance $C_M$ is in the range of $C_M \approx 2$ pF . . . 500 pF.

* * * * *